United States Patent
Klun

(10) Patent No.: US 7,523,646 B2
(45) Date of Patent: Apr. 28, 2009

(54) FILTERING AND MEASURING APPARATUS FOR OILS

(75) Inventor: Wolfgang Klun, Inglostadt (DE)

(73) Assignee: Ebro Electronics GmbH & Co. KG, Inglostadt (DE)

( * ) Notice: Subject to any disclaimer, the term of this patent is extended or adjusted under 35 U.S.C. 154(b) by 366 days.

(21) Appl. No.: 10/576,886

(22) PCT Filed: Oct. 25, 2004

(86) PCT No.: PCT/EP2004/052651
§ 371 (c)(1),
(2), (4) Date: Apr. 24, 2006

(87) PCT Pub. No.: WO2005/040788
PCT Pub. Date: May 6, 2005

(65) Prior Publication Data
US 2007/0040559 A1 Feb. 22, 2007

(30) Foreign Application Priority Data
Oct. 23, 2003 (DE) ................. 103 49 741

(51) Int. Cl.
*G01N 33/26* (2006.01)
*B01D 35/30* (2006.01)
(52) U.S. Cl. ............ 73/53.05; 73/53.07; 73/54.01; 210/85
(58) Field of Classification Search ........ 73/53.05, 73/53.06, 53.07; 210/85, 92, 93, 94, 95
See application file for complete search history.

(56) References Cited

U.S. PATENT DOCUMENTS 5,023,133 A 6/1991 Yodice et al.

(Continued)

FOREIGN PATENT DOCUMENTS

DE 69810288 2/2000

(Continued)

OTHER PUBLICATIONS

Hardman, W. et al.; "A Helicopter Powertrain Diagnostics and Prognostics Demonstration"; Aerospace Conference, 2000 Proceedings IEEE; Big Sky, MT, USA; 03/18-25/2000; pp. 355-365.

(Continued)

*Primary Examiner*—David A. Rogers
(74) *Attorney, Agent, or Firm*—Fish & Richardson P.C.

(57) ABSTRACT

Disclosed is a method for measuring at least one state characteristic of oil or fat in a device that uses oil or fat and is provided with a filtering apparatus (1; 101) comprising a filter housing (2) and at least one filter element (7) which is inserted thereinto. According to said method, at least one sensor (35, 36; 135; 235) of a measuring device (30; 130; 230) is introduced into a measurement space (8; 208) located in the oil or fat circuit in order to measure at least one state characteristic of the oil or fat, and the measured values thereof are evaluated using measuring electronics (32; 132) that are connected to the at least one sensor (35, 36; 135; 235). The inventive method is characterized in that a microfilter element, ultrafilter element, or nanofilter element (7) is used as a filter element. Also disclosed are a corresponding filtering apparatus (1) and a correspondingly configured measuring device (130).

3 Claims, 4 Drawing Sheets

U.S. PATENT DOCUMENTS

| | | | |
|---|---|---|---|
| 5,238,085 A * | 8/1993 | Engelmann | 184/1.5 |
| 6,770,196 B2 * | 8/2004 | Wall | 210/238 |
| 2003/0046985 A1 | 3/2003 | Schoess | |
| 2003/0179002 A1 * | 9/2003 | Beylich et al. | 324/663 |
| 2004/0011715 A1 * | 1/2004 | Assion | 210/136 |

FOREIGN PATENT DOCUMENTS

| | | |
|---|---|---|
| DE | 10015516 | 11/2000 |
| DE | 101 03 532 | 8/2001 |
| DE | 100 25 690 | 11/2001 |
| DE | 10137308 | 2/2003 |
| DE | 101 63 760 | 7/2003 |
| DE | 102 08 600 | 9/2003 |
| EP | 0980522 | 2/2000 |

OTHER PUBLICATIONS

International Search Report issued in PCT/EP2004/052651 and Written Opinion of the International Searching Authority issued Apr. 27, 2005; 19 pages.

Search Report issued in counterpart German Application No. 10349741.2; May 26, 2004; 3 pages.

* cited by examiner

FILTERING AND MEASURING APPARATUS FOR OILS

CROSS REFERENCE TO RELATED APPLICATIONS

This application is a National Stage application under 35 U.S.C. §371 that claims the benefit of PCT/EP2004/052651, filed Oct. 25, 2004, which claims the benefit of German Patent Application Serial No. 10349741.2 filed Oct. 23, 2003. This application claims priority to International Application Serial No. PCT/EP2004/052651 and German Patent Application Serial No. 10349741.2.

TECHNICAL FIELD

The invention relates to a device and method for filtering and measuring a characteristic of oil and fats.

BACKGROUND

The determination of the state characteristics of oils (including fats but not limited to use for food preparation) is in demand in many fields. In the engine, hydraulics, transmission and turbine fields, especially in the area of motor vehicles, for example, a great need exists to measure in particular the oil quality as well as the oil temperature of the oil in circulation. Oil can, for example, oxidize in the engine of a motor vehicle due to the air penetrating the crankcase, so that in the process acids can form. Separated oleoresins and asphalts as well as street dust, metallic abraded particles and dissolved combustion residues sludge up the oil. The circulation of oil can be additionally impeded by condensation water and sometimes coolant. As a result the oil quality and oil degradation make it possible to determine whether an oil change is necessary to conserve the machine components.

A known oil sensor of TEMIC company is able to measure the dielectric constant, the level as well as the temperature of the oil in an oil pan of a motor vehicle. For this purpose the sensor cell exhibits two cylindrical capacitors, of which one is completely immersed in the oil. Its capacity depends on the dielectric constant of the oil. The second capacitor is located in a position at which the oil state can be determined between the expected maximum and minimum level. The capacity of the second capacitor depends on the dielectric constant of the oil and the level in the oil pan. The sensor cell can be mounted in the oil pan with the help of a mechanical adapter. The sensor cell is connected via electronic cable to measuring electronics outside of the oil pan. The sensor cell is for this purpose guided through the oil fillers and screwed to the filler with the help of the mechanical adapter.

A disadvantage of the known oil sensor is the fact that its operation is relatively awkward. The sensor must be removed prior to the refilling of the oil. A further disadvantage consists in the fact that the oil in the oil pan does not necessarily represent the oil that is in circulation and therefore does not furnish a clear picture of the actual lubricant. The metal of the oil pan as well as that of the crankshaft can constitute an additional problem which can lead to inductive currents that influence the measuring accuracy.

In addition, from DE 101 03 532 A1 as well as from DE 100 25 690 A1 it is known to arrange a sensor close to the inside wall of a filter housing of an oil cycle. In the case of these known arrangements, among other things, the accessibility to the sensor is restricted or the expenditure for replacing the sensor is quite high. Similarly, it holds true also for the filtering apparatus disclosed in US 2003/0046985 A1, which discloses a cylindrical linear arrangement of several electrodes at the inside wall of a filter housing. Here too the accessibility and handling of the measuring device is not easy. In addition the measuring accuracy of these oil sensors is not optimum.

DE 102 08 600 A1 describes a sensor integrated in an oil filter which can only be replaced in conjunction with replacement of the oil filter. This device is correspondingly expensive and not to be favored in particular due to cost aspects.

U.S. Pat. No. 5,023,133 discloses an oil filter with a hollow cylindrical filter element into whose interior an acid sensor is placed. From the rim of the filter housing wires are conducted to an ohmmeter. This sensor is neither easily accessible nor easily replaceable.

In addition, precise measurement of the oil state characteristics is not possible with any of the known measuring devices.

In other fields, in particular in the field of food, the measurement of state characteristics of fats is desirable or even prescribed by law. Thus there is a great need for example in the case of frying fats for a simple and precise means of determining their quality as well as their temperature or other measurable fat characteristics.

SUMMARY

The present invention may be used with lubricating oils and fats used for food preparation. As used herein, the term "oil" includes oils and fats.

In accordance with the inventive method it was recognized that a highly precise measurement of the oil state can be performed when the material to be measured has been very finely filtered. Therefore, the filter element is constructed in the oil circulation as a microfilter, ultrafilter or nanofilter element, i.e., particles with a size below 10 µm are filtered out of the stream. Nominally a microfilter (also know as a particulate filter) filters particles greater than 1 µm, an ultrafilter filters particles greater than 0.1 µm and nanofilter filters particles greater than 0.01 µm. In routine operation microfilters are capable of filtering out particles of a size of approximately 3 µm and smaller from the oil stream.

The filter material of said filter is preferably cellulose, fiberglass and/or ceramic. It turns out that with an oil filtered in such manner, the sensor is significantly better protected from "weathering", so that the precision of the measurements can be significantly increased. Similarly the acid formation in the oil can be severely reduced because the inventive use of a microfilter removes moisture from the oil and consequently less acid acetate forms. The service life of the oil is also extended as a result of this measure. In addition, it turns out that very small metal particles, in which no weight has been attributed in the known measurements, damage the sensor, because they can be attracted by said sensor. In particular, if the sensor is a capacitor, the measurement results were not accurate, which is now prevented as a result of the use of the microfilter for filtering out these small metal particles.

In accordance with one design embodiment, the filtering apparatus is arranged in a bypass flow of an oil cycle, wherein as a rule additionally a full flow filtering apparatus is provided. In the case of such a configuration a high protection against wear and tear of the full flow filtering apparatus is guaranteed, while the bypass flow filtering apparatus provides an extremely intensive cleansing of the oil. By using a bypass flow filtering apparatus in particular the oil quality can be determined quite accurately and quite easily, since the oil is very finely filtered after a few passes through the circulation and therefore provides an accurate reference for a possible oil change. In this connection it is expedient if the sensor, of which there is at least one, is calibrated for the determination of the oil quality to new oil quality, i.e., the deviation of the current oil quality is determined against the new oil quality.

In the case of the bypass flow arrangement of the filtering apparatus the actual oil quality can consequently be precisely determined, in order to perform an oil change at the right time. In this connection the microfilter offers the advantage that the oil maintains a very long service life.

In accordance with another design embodiment, an oil cycle engine lubrication measurement is made in the interior of the filter housing of the filtering apparatus. The filter housing is constructed to be easily accessible, since as a standard feature the filter element in the filter housing must be replaced at great time intervals. In connection with this there is the advantage that measurements—in the case of an engine with oil lubrication—are possible in routine operation. For example the filtering apparatus can be separated from the oil cycle after a certain time when the engine is running, so that oil is located in the filter housing and then the measurement can be made with a hand device. The oil, which preferably continues to be pumped in the oil delivery cycle, can during this time reach the lubricating points by means of a bypass. In an alternative which is also discussed further below, a sensor is permanently mounted in the filter housing for this purpose. As a result, information is obtained continuously with regard to the at least one state characteristic of the oil actually circulating in the oil cycle.

It turns out that the inventive method is applicable to engines which are operated with RME (Rape methyl ester) or biodiesel. This fuel contains both linolic acid as well as linoleum acid, wherein the former is a dirt dissolver and the latter acts as an adhesive. At oil lubricating points the dirt particles polymerize in oil with the linoleum acid of the biodiesel, so that in accordance with the invention the oil is very finely filtered so that the sticking of the lubricating points and the lubricating oil line channels can be prevented. In accordance with the inventive method checking this filtration in the oil filter housing is easily possible.

The inventive filtering apparatus is characterized by a filter element which is constructed as a microfilter, particulate filter, ultrafilter or nanofilter element, as a result of which the aforementioned advantages result. Nominally microfilters or particulate filters remove dirt particles of a particle size down to about 1 µm; however, in operation they remove particles up to a size of a few µm.

A sensor placed in the measurement space is preferably surrounded by filter material of the previously mentioned microfilter, ultrafilter or nanofilter element. It is preferred that the sensor is placed in the oil flow if at all possible. This is in particular the case when the filter element is constructed as a hollow cylinder and the oil flows from the inside to the outside or from the outside to the inside. This guarantees that the at least one state characteristic of the oil circulated in the circuit can be measured in a simple manner with the machine running.

Expediently, for the aforementioned purpose a shut-off device is provided upstream from the inlet for the oil in the filter housing. This shut-off device can be operated manually in order to actively shut off the oil line and be able to perform the measurement. The shut-off device can advantageously be designed as a valve or as a shut-off cock. While in this way the oil actually reaching the oil circuit can be measured, a measurement in the oil pan could provide a false picture, since the composition of the oil in the pan can be different than the composition of the oil in the circuit.

The described manual operating shut-off device can in particular find application when a hand device is to be used—preferably the device described in DE 100 15 516 A1 and DE 101 63 760, which exhibits an interdigital capacitor as a sensor—to temporarily measure the oil, for example at the test bench of an auto repair shop and in particular with a running engine or turbine. In this case the motor vehicle does not have to be equipped with a permanent sensor, so that this constitutes a cost-effective variant. Preferably at least the majority of the measuring electronics are integrated in the housing of the hand-operated measuring device which is connected to the sensor via an attachment (see DE 101 63 760).

An interface can be mounted on the housing of the hand-operated measuring device, with whose help data, which is for example stored in the measuring electronics of the measuring device, can be read out (data logger function) and also data can be input into the measuring device from the outside, for example from a PC.

Regardless of whether the state characteristic of the oil is measured temporarily or as a stationary measurement, an insertion opening on the filter housing is provided, through which the sensor can be mounted in the measurement space temporarily or stationary. In this embodiment the insertion opening is constructed in the housing cover.

As an alternative, the entire insertion opening of the filter housing to be closed by the housing cover is suitable for inserting the sensor. In both cases the corresponding seal of the insertion opening can preferably be quickly removed in order to insert the sensor into the measurement space in the filter housing.

In the case of the usage of a filter element with—preferably central—hollow space the sensor can be expediently introduced into a measurement space in this central hollow space, preferably through an insertion opening on the topside of the filtering apparatus and in this connection in particular through an insertion opening provided in a housing cover. The filter housing is in this connection preferably arranged essentially upright. In the case of this embodiment, sufficient space for using the measuring device is available when the inlet and outlet are moreover arranged on the underside or on a side wall of the housing. In an expedient embodiment in this regard a hollow cylindrical filter element is used, which especially preferably is constructed of pure cellulose to bind the water from the oil. Such a microfilter or particulate filter element can nominally filter out particles in the size of 1 µm.

A particularly simple operation of the filtering apparatus in interaction with the measuring device results when the insertion opening is essentially aligned with the measurement space.

The measuring device for temporary measurement can be supported on the edge of the insertion opening of the filter housing so that another unit of the measuring device to be grasped by the user protrudes from the filter housing. Such a design then requires only access to the opening of the insertion opening and the insertion and support of the measuring device so that the sensor comes into contact with the oil in the filter housing.

The insertion opening may be closed by a closing element, e.g. a screw unit, in particular a screw, which for example is arranged in the housing cover. For temporary measurement, this screw may then be removed in order to insert the sensor into the filter housing. A wide display and handle unit with a housing or another correspondingly wide constructed section on the hand measuring device can support itself on the outer edge of the insertion opening, while the sensor submerges into the oil.

In the case of an embodiment comprising a stationary measuring device, a first retaining section on the housing cover is provided for direct or indirect coupling to a second retaining section of an inventive measuring device. In this connection the opportunity presents itself for frictional coupling of the first and second retaining sections.

In accordance with one embodiment the first retaining section is constructed on the insertion opening of the housing cover previously mentioned and comprises for example an internal thread. Correspondingly the measuring device can (without the measuring electronics) be screwed into the insertion opening with a corresponding external thread and simultaneously close said insertion opening. Then wires are conducted to the outside to the measuring electronics of the measuring device. The named external thread is preferably provided on the named closing element, wherein the measuring device can be or is frictionally and/or positively coupled to its underside. This arrangement corresponds to a direct or indirect coupling of the measuring device to the filter housing.

In the case of a frictional coupling of sensor and closing element both are preferably removed from the filtering apparatus with a handle in order to replace the filter element, clean the sensor or replace the sensor/closing element unit.

As an alternative, the insertion opening can be closed with a seal that is not connected to the measuring device, wherein the named lines however are expediently guided through preferably sealed channels through the seal out of the filter housing. The measuring device is in this connection separated from the closing element on the housing cover and perhaps even arranged on the insertion opening, for example by means of a specially adapted suspension system.

The measurement space is preferably located at the height of the lower half of the filter element, in order to guarantee a secure immersion of the sensor into the oil. In addition, for the same reason it is expedient if the at least one sensor can be placed in the region of the lower edge of the filter element.

The measurement space in the filter housing is expediently provided in the proximity of the inlet or the outlet. In the first case the oil runs first past the sensor and then through the filter, in the second case it happens the other way around. Since the oil in particular in the case of a running engine or turbine is fed several times through the filter element, the oil quality in the case of both designs is essentially the same, so that the measured values in the two named cases do not differ essentially from one another. Here too the advantage arises that the oil that is actually in the oil circuit is measured and not the oil in the oil pan.

The at least one inlet and/or the at least one outlet are preferably arranged at the underside of the filter housing. The oil proceeds preferably first vertically from bottom to top through the filter housing in order to exit the filter housing through the outlet again after changing directions. On the way up and/or down, the oil passes through the filter element.

In accordance with an expedient design of the invention at least one sensor can be inserted or installed both in the region of the outlet as well as also in the region of the inlet of the filter housing, so that—for example in the field of airplanes—the filter efficiency of the filtering apparatus can be determined.

The inventive measuring device is expediently constructed in such a way that one or more state characteristics of the oil can be measured with it, thus for example their dielectric constant, the viscosity, the pH value, TAN values (total acid number), TBN values (total base number), temperature, PC values (polar compounds) and/or FFA values (free fatty acids). In particular the dielectric constant gives information about the quality of the oil. The opportunity presents itself to construct the sensor correspondingly as a capacitor, expediently as an interdigital capacitor (IDK). Reference is made to the publications DE 100 15 516 A1 and DE 101 63 760 A1 of the applicant. Such a digital capacitor can accordingly find application both for the measurement by means of a hand measuring device (see DE 100 15 516 A1 and DE 101 63 760 A1) as well as for stationary measurement by coupling the measuring device with the filter housing cover.

In the case of the free fatty acids (FFA) these can be measured either via chemical or via physical methods. The TAN and/or TBN values are expediently measured with ion-sensitive semi-conductor sensors. The pH value can be measured preferably with a glass electrode or with an ion-sensitive semi-conductor sensor. The viscosity can be expediently measured with a surface sensor (SAW=surface acoustic wave technology). In the case of several sensors these are expediently integrated, for example arranged on a ceramic plate.

In accordance with one design the inventive device is constructed as a motor vehicle, wherein the corresponding engine, hydraulics, transmission and/or turbine parts are supplied via an oil circuit. The inventive method can be performed with the assistance of the inventive filtering apparatus, either—in the case of an engine-operated motor vehicle—with the assistance of a hand measuring device to be used only with a standing motor vehicle in the case of a preferably running engine or a measuring device remaining stationary in the filter housing in the case of a standing (with preferably running engine) or a driving motor vehicle.

The driver may be informed with the help of a means of communication about the measured values (in raw or evaluated form). The driver does not have to actively intervene in order to obtain the information. The display unit provided for this purpose can display the information on an acoustical or optical basis. The measuring electronics of the measuring device, which services the purpose of preparation and if necessary evaluation of the measured values is in this connection connected to the display unit for example via radio or a field bus system.

In the case of an optical reproduction it is expedient if the information is displayed in the field of view of the driver, e.g. on the instrument panel or the windshield. The driver can consequently in the case of the stationary measuring device be informed during the drive about the oil state and other oil parameters and in particular be alerted about critical values.

In accordance with a corresponding improvement of the invention various colored signaling devices can be used to indicate the state of the oil. In the case of a signaling device flashing green the driver is notified that the oil exhibits an uncritical state. A yellow or red signal informs the driver that the oil state is approaching a critical phase or has already reached an alarm state.

In another embodiment of the invention the inventive device is constructed as a deep fryer for the field of food preparation, wherein the oil (fat) in the deep fryer can be measured with the invention.

Expedient improvements of the invention are characterized by the features of the dependent claims.

The details of one or more embodiments of the invention are set forth in the accompanying drawings and the description below. Other features, objects, and advantages of the invention will be apparent from the description and drawings, and from the claims.

DESCRIPTION OF DRAWINGS

The invention will be explained in greater detail with the help of the figures.

Like reference symbols in the various drawings indicate like elements.

DETAILED DESCRIPTION

Figure 1:
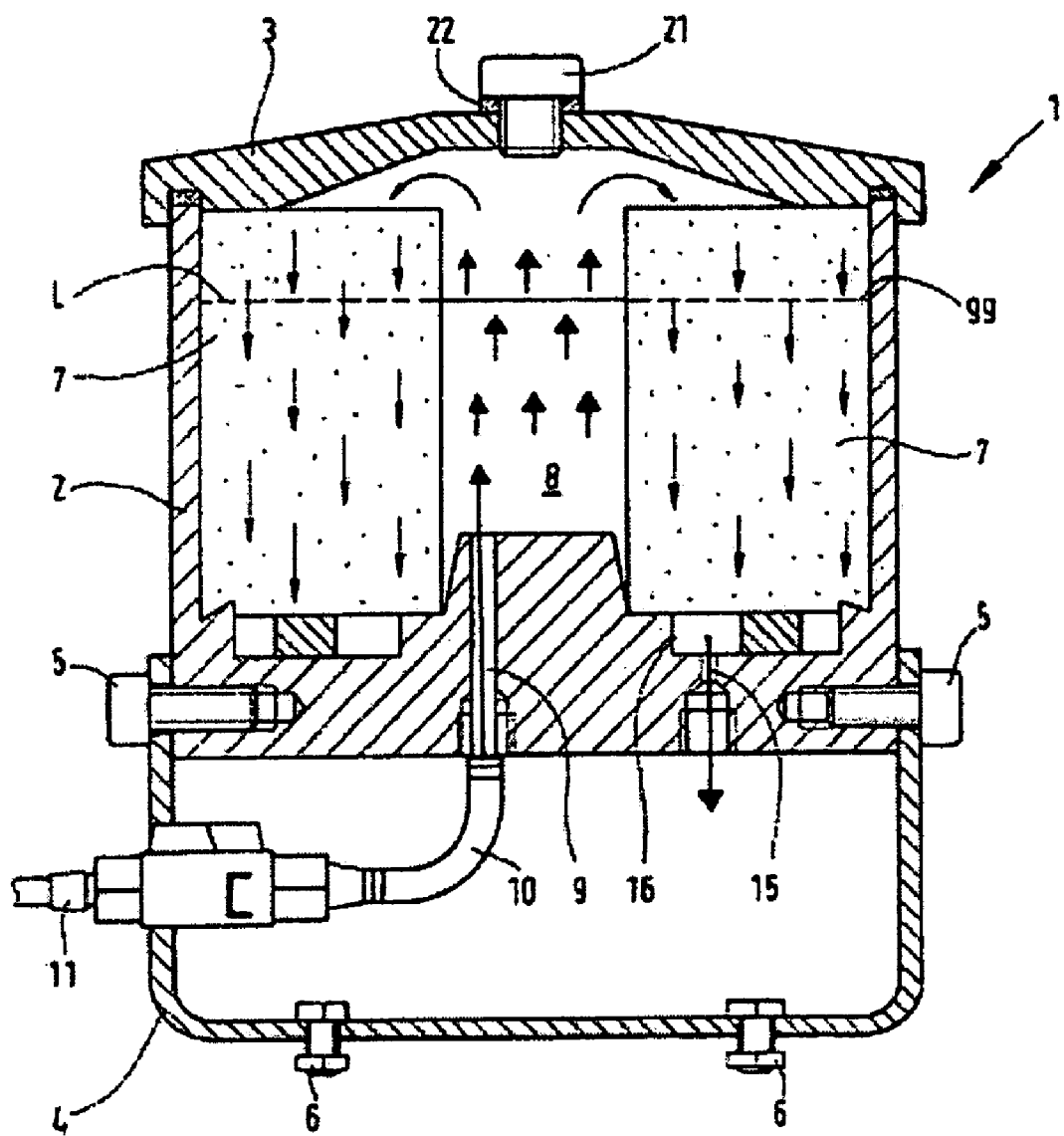
FIG. 1 illustrates a lateral cross-sectional view of a filtering apparatus.

Referring now to FIG. 1, a filtering apparatus 1 is shown in cut lateral view, which exhibits a cup-type filter housing 2 with a housing cover 3 disposed on the topside of housing 2. The filtering apparatus 1 is constructed essentially symmetrical to its longitudinal axis and is depicted in upright position. Underneath the filter housing 2 a connecting piece 4 in a u-shaped configuration is connected via screws 5 to the filter housing 2. Screws 6 for mounting to automotive body sheet metal or the like are provided on the underside of the piece 4.

In the interior of the filter housing 2 a hollow cylinder-shaped, replaceable filter element 7 is inserted, which is constructed as an axial rolled microfilter or particulate filter element made of cellulose with an exterior stocking-shaped cover. Such a microfilter or particulate filter element can nominally filter out particles in the size of 1 μm. In operation these filters generally filter particles of the size of approximately 2.5 μm and larger.

An inlet 9 constructed as a borehole flows into the measurement space 8 enclosed by the filter element 7, said inlet being fed by a feed pipe 10. On the other end of the feed pipe 10 a shut-off cock 11 is fastened to a side wall of the piece 4. Cock 11 is the means by which the oil supply to the filtering apparatus 1 can be interrupted. In addition, underneath the filter element 7 an outlet 15 for the filtered oil is provided, which after passing through the filter element 7 first flows into a snap ring groove 16 before it is forced by the following oil to the outlet 15 (the drain for the filtered oil is not shown). In accordance with this structure oil from below essentially arrives centrally in the measurement space 8 and is rerouted at the inner wall of the housing cover 3 to the outside, in order to run from above through the filter element 5 and subsequently leave the filter housing 2 (see arrows). The oil level shown in partially dotted lines is indicated by the reference symbol L. Centrally in the housing cover 3 is an insertion opening 20 aligned with the measurement space 8. An internal thread is provided, in which a hexagon screw 21 with a sealing ring 22 is positioned.

Figure 2:
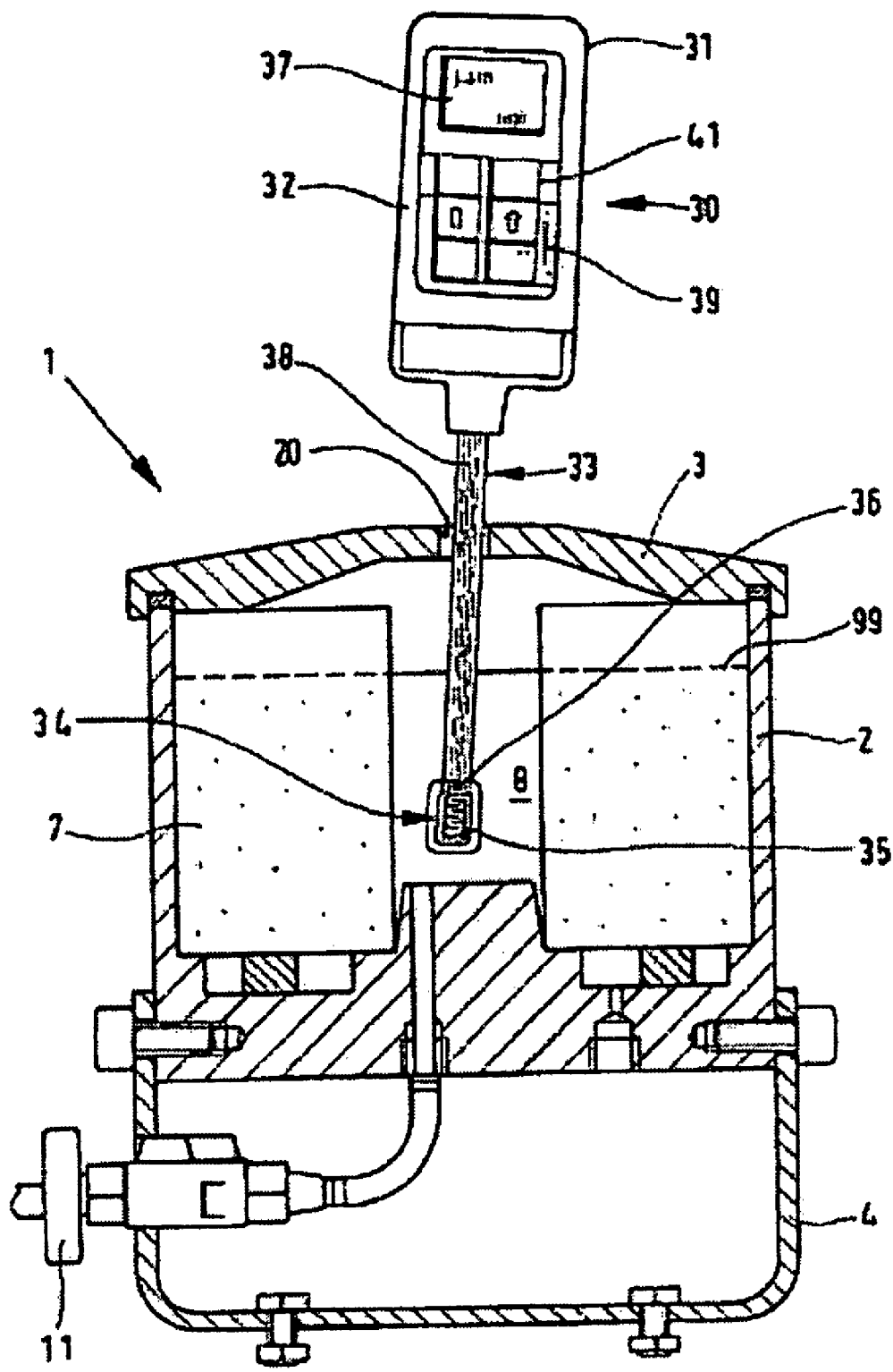
FIG. 2 illustrates a cross-sectional view of the filtering apparatus of FIG. 1 with a hand measuring device.

Referring now to FIG. 2, the screw 21 of FIG. 1 is removed and a hand measuring device 30 is inserted into the opening 20. The measuring device 30 in the embodiment shown can be constructed corresponding to DE 100 15 516 A1 and/or DE 101 63 760 A1, i.e. it comprises a housing 31 with measuring electronics 32 accommodated therein. The housing 31 is connected via an oblong attachment 33 to a measuring head 34, upon which a sensor 35 is mounted. The sensor 35 in the illustrated embodiment is constructed as a capacitor made of fine gold wires meshed within one another (see DE 101 63 760 A1). The very finely filtered oil by means of the filter element can be very precisely measured by means of this capacitor. Additionally, because the larger metal particles were filtered out of the oil, the service life of the sensor 35 is increased.

Additionally, a temperature sensor 36 is additionally arranged in the proximity of the capacitor on the measuring head 34. The sensors 35, 36 are connected to the measuring electronics 32 via lines that run in or on the attachment 33. Additionally, an interface 39 is mounted on the housing 31 via the interface 39. Data stored in the measuring electronics 32 can be read out and also data from the outside, for example from a PC, can be input into the measuring device 30. A keyboard 41 is also provided on the housing 31, by means of which the selection or calibration commands for example can be entered, as well as by means of which the measuring device 30 can be switched on and off.

To measure the dielectric constant of the oil in the filter housing 2 and if necessary its temperature the shut-off cock 11 is first manually turned into closing position, then the hexagon screw 21 is unscrewed from the insertion opening 20 and then the measuring device 30 is inserted into the measurement space 8 in such a way that the measuring head 34 is submerged into the oil. The oil level is marked with the reference symbol 99. Information is displayed on a display unit 37 on the housing 31, which is simultaneously constructed for handling by an operator, said information which can comprise the measured dielectric constant and/or an oil quality deduced from this or if necessary the temperature. Alternatively, or in addition, by means of color signaling devices on the housing 31 (for example using the colors green, yellow and red) a good, soon to be critical as well as a critical quality state of the oil is displayed. Acoustic signals can be output as an alternative or in addition, e.g. a warning beep for critical oil state.

After the measurement, the measuring device 30 is again removed from the filter housing 2, the screw 21 is replaced and the shut-off cock 11 is opened.

If the previously described filtering apparatus 1 is inserted into an oil circuit for the lubrication of an engine, the named measurement can be performed with a running engine. Preferably, the shut-off cock 11 is not closed until the filter housing 2 is filled with oil and preferably the oil to be measured has passed through the oil circuit a few times already. In the case of a closed shut-off cock 11 the additionally pumped oil circulates outside of the filtering apparatus 1 via for example an overflow line not shown or a main flow line in the circuit and consequently reaches the lubricating points.

Figure 3:
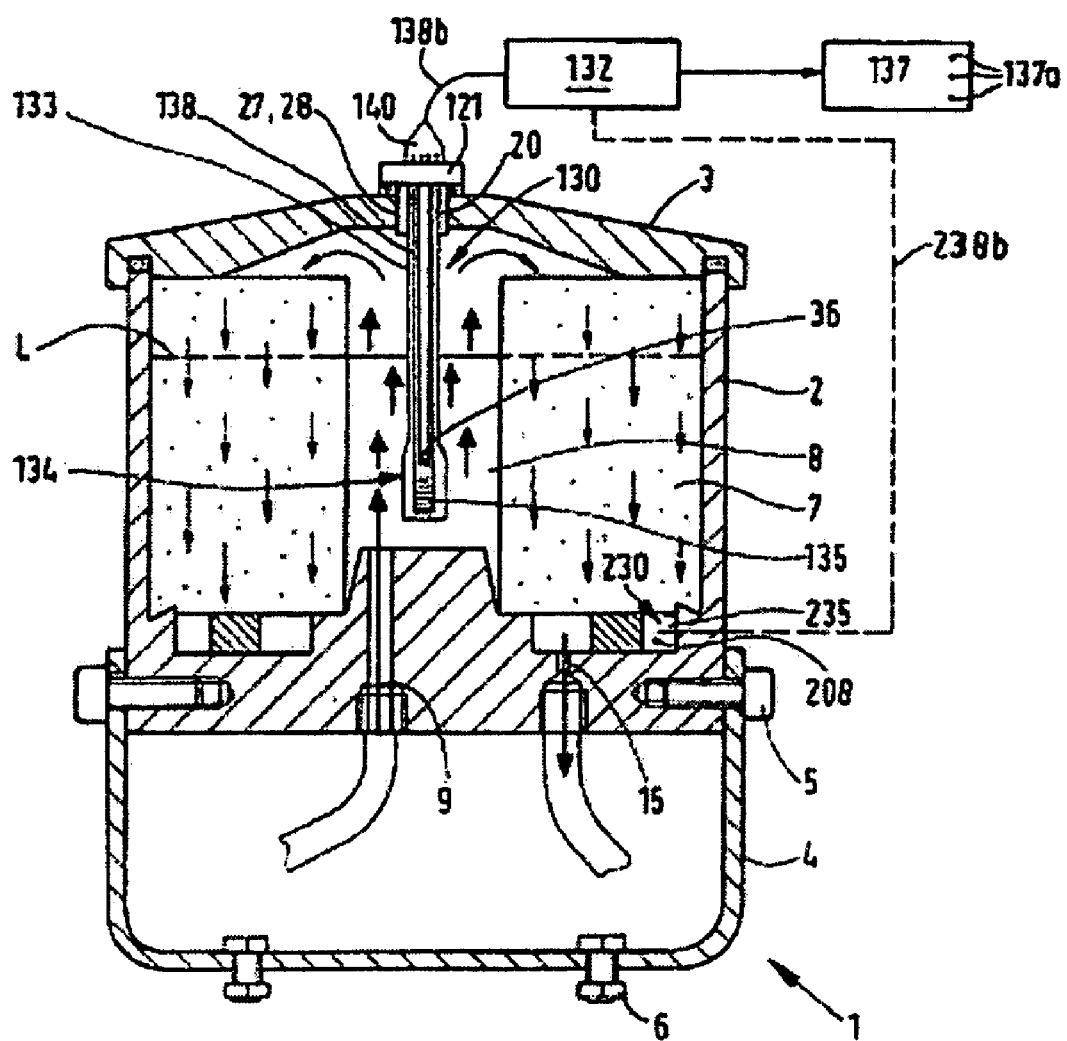
FIG. 3 illustrates a cross-sectional view of another embodiment of a filtering apparatus inserted therein with a stationary measuring device disposed therein.

A second inventive embodiment 101 is reproduced in FIG. 3 in cut lateral view. The same reference symbols in FIGS. 1 through 3 mark the same components. In the design in accordance with FIG. 3 in place of the screw 21 (see FIGS. 1 and 2) a measuring device 130 is screwed into the insertion opening 20. The internal thread of the insertion opening 20 serves as a first retaining section 27. A second retaining section 28 corresponding to the first one in the form of an external thread is provided with a closing element 121 coupled to the measuring device 130. The measuring device 130 is in this connection may be frictionally coupled to the closing element 121, wherein the closing element 121 serves the purpose of sealing the insertion opening 20. The measuring device 130 can in accordance with an alternative be non-separably (i.e. not without destruction) coupled to the closing element 121. Alternatively, the housing of the measuring device may be formed integrally with the closing element.

The measuring device 130 can in principle be constructed similar to the measuring device in accordance with FIGS. 1 and 2. The measuring head 134 projects at an attachment 133 into the measurement space 8 in the filter housing 2. Lines 138a, 138b connect the sensors 135 (capacitor) and if necessary 136 (temperature sensor) to the measuring electronics 132. The lines 138a proceed in filter housing 2 and end at the topside of the closing element 121 in plug contacts. A plug 140 is plugged into these contacts, whose lines 138b are conducted to the measuring electronics 132. The measured values are prepared and evaluated there and the corresponding information about the oil quality and temperature for example is reproduced on the instrument panel of the motor vehicle, upon which color signaling devices 137a can be arranged with different colors.

The measuring head 134 with the sensors (135 and 136) remains in the filter housing 2 and can also furnish information during the drive about the state and temperature of the motor oil.

In FIG. 3 an additional measuring device 230 with at least one sensor 235 is stationarily disposed into a measurement space 208, wherein the sensor 235 is arranged in the region of the outlet 15. Here the same statements apply as for the measuring device 130. The measuring device 230 serves the purpose of measurement of the state of the oil at the outlet, in order to compare the results with the help of the measuring electronics 132—after transferring the measured values by means of line 238b—to those of the measuring device 130 disposed proximal to the inlet 9. This information is particularly in demand in the field of aviation.

Figure 4:
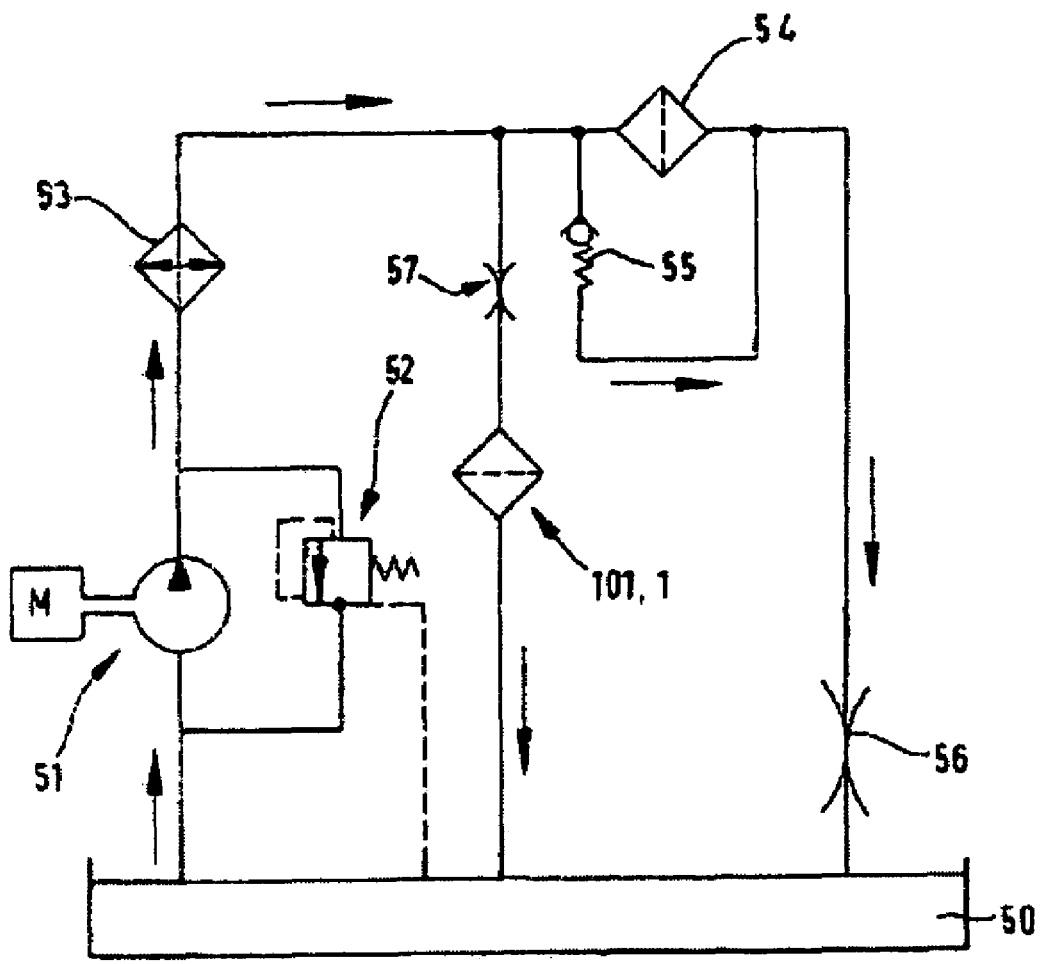
FIG. 4 illustrates a hydraulics schematic of an oil circuit with a full flow and a bypass flow filter combination.

In FIG. 4 one possible use of the measuring devices 30 and 130 is schematically illustrated. An oil pan 56 is provided in an oil circuit with lubricating points 56, from which said oil pan oil is supplied by means of an oil pump 51 via an oil cooler 53 to a main flow filtering apparatus 54 and then to the lubricating points 56. An excess pressure valve 52 is provided for oil pressure that is too high. In the case of a plugged main flow filtering apparatus 54, in addition a bypass flow valve 55 guarantees that oil can reach the lubricating points 56 in spite of this. In a bypass flow circuit a bypass flow filtering apparatus 1 or 101 is provided, to which a throttle 57 is connected in series. The bypass flow filtering apparatus 1 or 101 provides for an extremely intensive cleansing of the oil. As a result it is guaranteed that the oil quality will remain very good over long periods of time and in addition with the help of the measuring device 1 or 101 it can be precisely determined when an oil change is actually necessary. It is then no longer necessary for example to resort to the kilometers that have been traveled, according to which—often too soon or also too late—an oil change is performed as a standard feature.

The invention has been explained for use in a motor vehicle (personal or truck, airplane, ship). The same applies in the measuring of fats, in particular in the field of food.

As used herein, the term oil includes either or both oils and fats.

Examples of one or more embodiments of the present invention have been illustrated and discussed in this specification; however, the claims are not limited to the disclosed embodiments.

A number of embodiments of the invention have been described. Nevertheless, it will be understood that various modifications may be made without departing from the spirit and scope of the invention.

The invention claimed is:

1. A filtering and measuring apparatus, said apparatus comprising:
    a filter housing with at least one inlet and one outlet;
    a removable housing cover adapted for replacement of the filter element;
    an oil filter element disposed in the filter housing, said element selected from the group of microfilters, ultra filters and nanofilters;
    at least one measurement space in the filter housing; and
    at least one sensor in a measuring device for the measurement of at least one characteristic of an oil located in the measurement space, wherein the measuring device is disposed in an insertion opening in the removable housing cover and wherein the insertion opening is adapted to be closed by a removable closing element and said removable closing element includes a first retaining section adapted for coupling to a second retaining section on the measuring device in order to position the at least one sensor stationary in the measurement space.

2. The method of measuring a characteristic of oil comprising:
    providing a filtering apparatus having a filter housing with at least one filter element inserted therein, said filter element selected from the group of microfilter, ultrafilter or nanofilter elements;
    temporarily inserting a hand held measuring device having at least one sensor into a measurement space located in the filter housing;
    measuring a dielectric constant of the oil using a capacitor;
    evaluating the measured dielectric constant using measuring electronics that are connected to the at least one sensor.

3. The method according to claim 2 wherein the step of inserting the measuring device further includes guiding the at least one sensor into the measurement space through an insertion opening in the housing.

* * * * *

UNITED STATES PATENT AND TRADEMARK OFFICE
CERTIFICATE OF CORRECTION

PATENT NO. : 7,523,646 B2  Page 1 of 1
APPLICATION NO. : 10/576886
DATED : April 28, 2009
INVENTOR(S) : Wolfgang Klun It is certified that error appears in the above-identified patent and that said Letters Patent is hereby corrected as shown below:

Title Page,
Item (73) Assignee – replace "Electronics" with -- Electronic --

Drawings – Sheet 3 of 4 (Figure 3) – replace reference numeral "138" with -- 138a --

Drawings – Sheet 3 of 4 (Figure 3) – replace reference numeral "1" with -- 101 --

In column 1, line 19 – replace "oil and fats" with -- oils and fats --

In column 2, line 35 – replace "know" with -- known --

In column 4, line 64 – replace "oil." with -- oil or fat. --

In column 5, lines 12-17 – delete "The named...........filter housing." and insert the same on Col. 5, Line 13 below "device" as a new paragraph In column 6, line 56 – replace "more embodiments" with -- more of the embodiments --

Signed and Sealed this

Fourteenth Day of July, 2009

JOHN DOLL
*Acting Director of the United States Patent and Trademark Office*